(12) United States Patent
Agrawal

(10) Patent No.: US 8,662,306 B2
(45) Date of Patent: Mar. 4, 2014

(54) UNIVERSAL CATHETER TRAY ASSEMBLY

(71) Applicant: Cook Medical Technologies LLC, Bloomington, IN (US)

(72) Inventor: Sony Agrawal, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/763,872

(22) Filed: Feb. 11, 2013

(65) Prior Publication Data

US 2013/0264239 A1 Oct. 10, 2013

Related U.S. Application Data

(60) Provisional application No. 61/620,092, filed on Apr. 4, 2012.

(51) Int. Cl.
*B65D 85/08* (2006.01)

(52) U.S. Cl.
USPC .......................... 206/571; 206/370; 206/459.5

(58) Field of Classification Search
USPC .............. 206/363, 364, 370, 459.5, 438, 477, 206/480, 483, 476, 571
See application file for complete search history.

(56) References Cited

U.S. PATENT DOCUMENTS

| 4,216,860 | A | * | 8/1980 | Heimann | 206/370 |
|---|---|---|---|---|---|
| 4,266,669 | A | * | 5/1981 | Watson | 206/564 |
| 4,779,727 | A | | 10/1988 | Taterka et al. | |
| 5,131,537 | A | | 7/1992 | Gonzalez | |
| 5,165,540 | A | | 11/1992 | Forney | |
| 5,318,543 | A | * | 6/1994 | Ross et al. | 604/170.01 |
| 5,320,223 | A | * | 6/1994 | Allen | 206/372 |
| 5,322,163 | A | | 6/1994 | Foos | |
| 5,947,296 | A | * | 9/1999 | Castora | 206/571 |
| 6,009,998 | A | | 1/2000 | Webinger | |
| 6,068,121 | A | | 5/2000 | McGlinch | |
| 7,410,053 | B2 | * | 8/2008 | Bowen et al. | 206/373 |
| 7,743,920 | B1 | * | 6/2010 | Lordo | 206/438 |
| 7,886,908 | B2 | * | 2/2011 | Farrar et al. | 206/370 |
| 2006/0011501 | A1 | * | 1/2006 | Itou et al. | 206/370 |
| 2010/0025273 | A1 | * | 2/2010 | Matsuda et al. | 206/370 |
| 2011/0284410 | A1 | | 11/2011 | Lockwood | |
| 2012/0150123 | A1 | * | 6/2012 | Lawrence et al. | 604/180 |
| 2013/0074450 | A1 | * | 3/2013 | Higham | 53/425 |

FOREIGN PATENT DOCUMENTS

EP 1616593 1/2006

* cited by examiner

*Primary Examiner* — Jacob K Ackun
(74) *Attorney, Agent, or Firm* — Liell & McNeil

(57) ABSTRACT

Different length and diameter size catheters may be packaged in a universal catheter tray assembly that utilizes identical base trays. Catheter size selectors, which include a size indicia formed therein, are snap connected to the base tray and define at least a portion of a catheter capture channel with an opening width corresponding to the size indicia. The universal catheter tray assembly is configured for packaging a catheter with a size corresponding to the size indicia and with any one of a plurality of tip shapes such that first and second segments of the catheter are confined in first and second catheter capture channels, respectively.

8 Claims, 3 Drawing Sheets

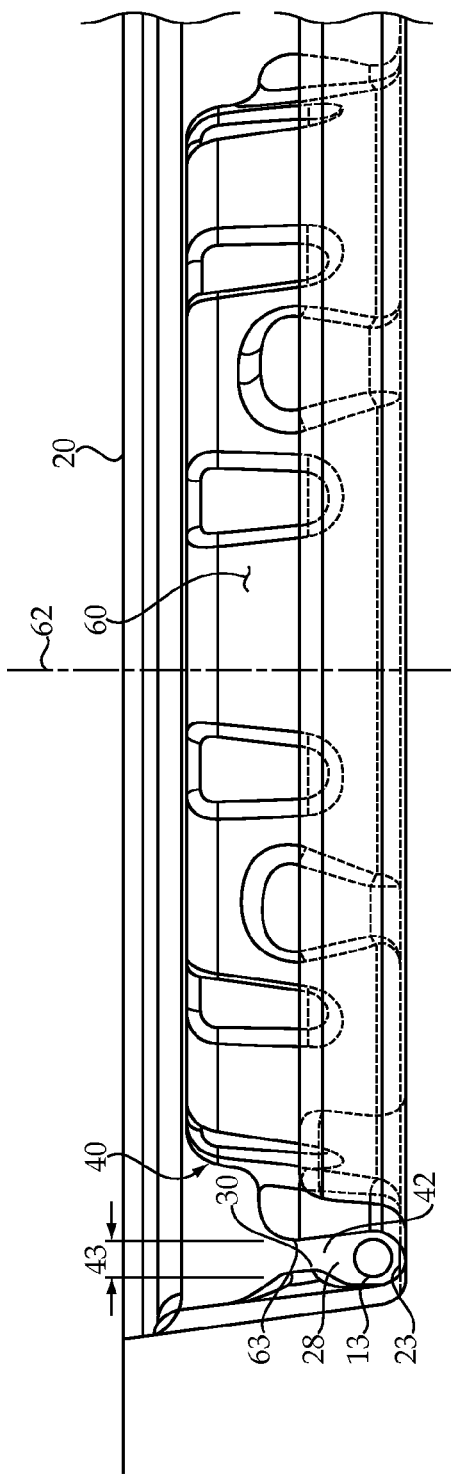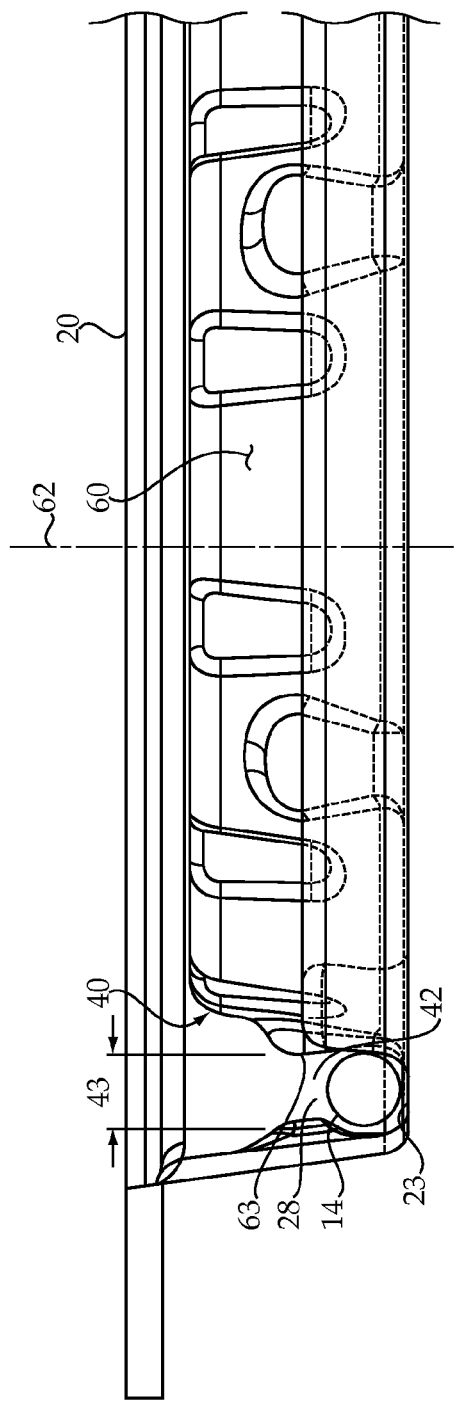

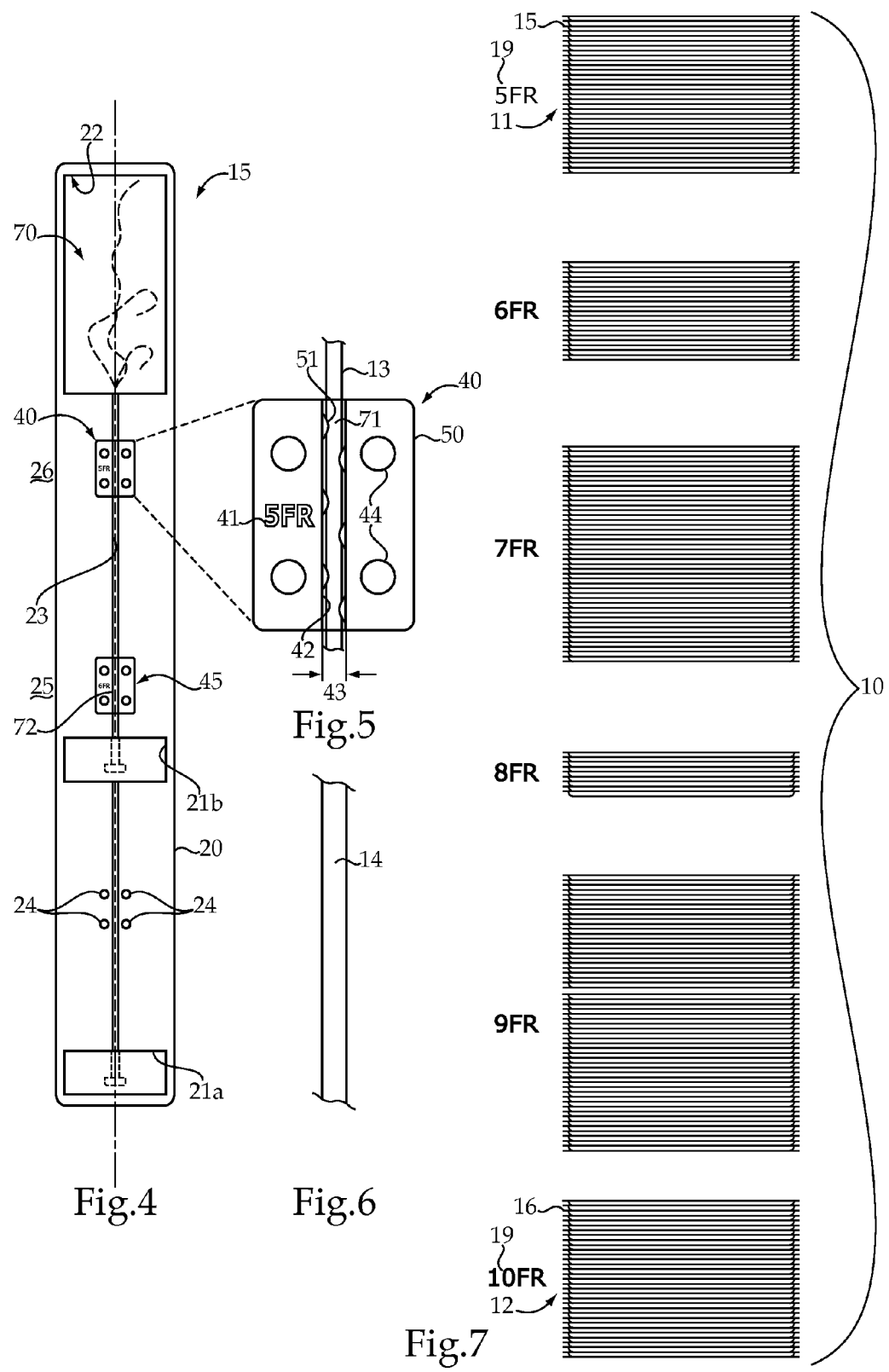

UNIVERSAL CATHETER TRAY ASSEMBLY

TECHNICAL FIELD

The present disclosure relates generally to packaging for catheters, and more particularly to a universal catheter tray assembly that can accommodate packaging for different diameter catheters.

BACKGROUND

Catheters are commercially available in a wide range of lengths, diameters and tip shapes. Because of this wide variety, different packaging has developed for different catheters. Because the volumes of catheters used in different sizes also varies greatly, the packaging costs for smaller runs of lesser used catheters can be relatively expensive. Many catheters are also packaged in various shaped trays often manufactured from a suitable transparent plastic, such as polyethylene trephthalate, which may include a dye to give the resulting product a pleasing hint of color, such as blue.

As stated, the use of multiple different trays or pouches for longer length catheters with different French diameter sizes has been the standard process in the industry for many years. Either an inner pouch with slat or an inner tray is first loaded and sealed, and then this subassembly is packaged in an outer pouch. The process not only takes time, but also adds cost of tooling and different tray sizes. The end user may have to open multiple pouches (in cases where pouches are used) in order to access all of the internal components. This practice can not only be time consuming but also wasteful.

In an effort to reduce the number of different trays necessary to accommodate a variety of different catheter sizes, U.S. Pat. No. 6,068,121 teaches a universal catheter tray manufactured in a unitary molding to include different recessed channel features to accommodate the catheters in a coiled arrangement.

The present disclosure is directed to solving one or more of the problems set forth above.

SUMMARY OF THE DISCLOSURE

A universal catheter tray assembly includes a base tray formed to include a fitting indentation separated from a shaped tip indentation by a groove, and further including a first snap connector at a first location along the groove and a second snap connector at a second location along the groove. A first catheter size selector, which includes a size indicia formed therein, is snap connected to the base tray at the first snap connector and defines at least a portion of a first catheter capture channel with an opening width corresponding to the size indicia. A second catheter size selector, which includes the size indicia formed therein, is snap connected to the base tray at the second snap connector and defines at least a portion of a second catheter capture channel with an opening width corresponding to the size indicia. The tray assembly is configured for packaging a catheter with a size corresponding to the size indicia and with one of a plurality of tip shapes such that first and second segments of the catheter are confined in the first and second catheter capture channels, respectively.

In another aspect, a method of packaging catheters includes selecting a small diameter catheter and constructing a first catheter tray assembly for the smaller diameter catheter by snap connecting first and second size selectors to a first base tray. A larger diameter catheter is selected and a second catheter tray assembly is constructed for the large diameter catheter by snap connecting third and fourth size selectors to a second base tray, which is identical to the first base tray.

In still another aspect, an inventory of packaged catheters includes a first and a second set of catheters. The first set of catheters consists of identical smaller diameter catheters, and the second set of catheters consists of identical larger diameter catheters. The first set of catheters is mounted in identical first catheter tray assemblies, and the second set of catheters are mounted in identical second catheter tray assemblies. Each of the first and second catheter tray assemblies has an identical base tray with selected catheter size selectors snap connected thereto.

BRIEF DESCRIPTION OF THE DRAWINGS

FIG. 2 is a sectioned view through a portion of the universal catheter tray assembly of FIG. 1 as viewed along section lines 2-2;

FIG. 3 is a sectioned view through a portion of the universal catheter tray assembly of FIG. 1 as viewed along section lines 3-3;

FIG. 4 is a top view of a universal catheter tray assembly according to another embodiment of the present disclosure;

FIG. 5 is an enlarged view of a catheter size selector from the universal catheter tray assembly of FIG. 4;

FIG. 6 is a top view of a segment of a larger diameter catheter according to the present disclosure; and FIG. 7 is a schematic view of an inventory of packaged catheters according to another aspect of the present disclosure.

DETAILED DESCRIPTION

Figure 1:
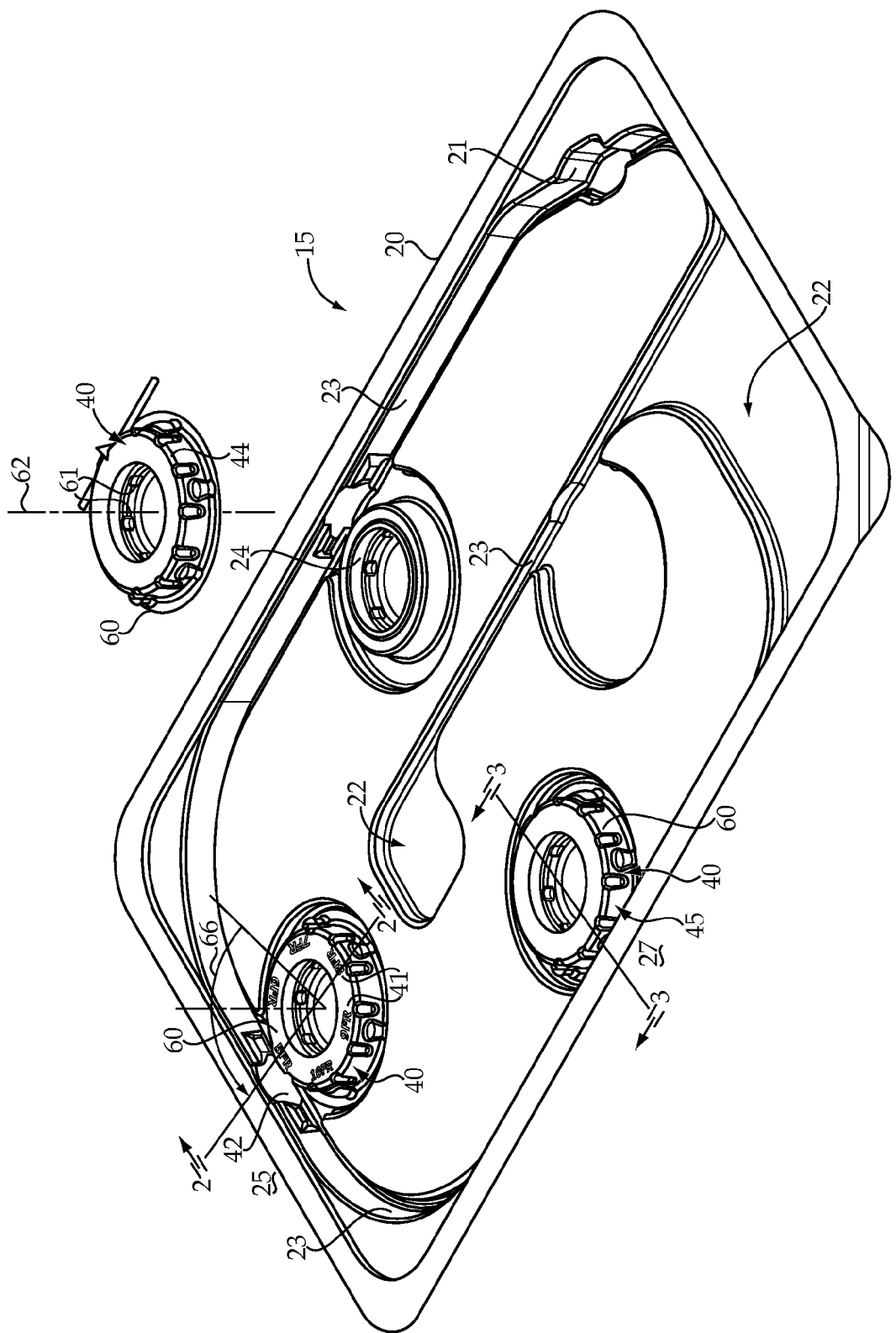
FIG. 1 is a partially exploded top perspective view of a universal catheter tray assembly according to the present disclosure.

Referring to FIGS. 1-3, a universal catheter tray assembly 15 includes a base tray 20 that is formed to include a fitting indentation 21 separated from a shaped tip indentation 22 by a groove 23. In this embodiment, groove 23 runs in a spiral between the fitting indentation 21 and the shaped tip indentation 22. Those skilled in the art will appreciate that catheters typically include a fitting attached at a proximal end, and includes a tip at the distal end that may have a preformed shape, such as a J, a pigtail or one of many many others known in the art. Base tray 20 is formed to include a plurality of snap connectors 24 that are distributed along groove 23. In particular, in the embodiment shown in FIG. 1, base tray 20 has three snap connectors 24 with one of the snap connectors located along groove 23 at a first location 25 and a second snap connector at a second location 27 along groove 23. A catheter size selector 40 is attached to each of the snap connectors 24 of base tray 20. The catheter size selectors are shown attached at locations 25 and 27, but a third catheter size selector is shown detached from base tray 20. Each of the catheter size selectors 40 are rotatable dials 60 that include size indicia 41 formed therein. Each of the size indicia corresponds to a different diameter size catheter on the French scale. For instance, in the illustrated embodiment, each of the rotatable dials 60 includes size indicia for 5, 6, 7, 8, 9 and 10 French catheters. When snap connected to the base tray, the respective catheter size selector 40 defines a portion of a catheter capture channel 42 with an opening width 43 corresponding to the adjacent size indicia 41. In the case of location 25, rotatable dial 60 is oriented at an angle 66 such that the five French indicia is adjacent groove 23 for an opening with 43 corresponding to a five French catheter.

A second catheter size selector 40 at location 27 is an identical rotatable dial 60 that is rotated to an angle corresponding to a ten French catheter. Although the catheter size selectors 40 of FIG. 1 are shown rotated to different angles to illustrate how the rotatable dials function, in practice, a catheter tray assembly 15 according to the present disclosure would be configured for packaging a single catheter with a size corresponding to one of the size indicia 41. For instance, all of the dials 60 of catheter tray assembly 15 might be rotated so that the five French indicia 41 would be adjacent spiral groove 23 at the respective snap connector locations. When set up for receiving the appropriate sized catheter. The catheter will be confined in the respective catheter capture channels 42 at each of the respective locations along groove 23.

Although not necessary, rotatable dials 60 may include a plurality of detents 61 around a rotation axis 62 that correspond to individual ones of the different catheter sizes associated with the size indicia 41. Thus, those skilled in the art will appreciate that the universal catheter tray assembly 15, with the illustrated rotatable dial 60, can be set up to package catheters in six different French sizes including 5, 6, 7, 8, 9 and 10 French catheters. As been shown in FIGS. 2 and 3, each of the catheter capture channels 42 is defined by the base tray 20 on one side and an edge 63 of the respective rotatable dial 60. For instance, base tray 20 might be formed to include an overhang 30 directly across from the respective rotatable dial 60. The edge 63 that defines the opposite side of the respective catheter capture channel 42 protrudes into groove 23 a distance sized to match the catheter size indicia 41 at that rotatable position of the respective dial 60. Thus, the edge 63 at the five French position is shown at FIG. 2 would protrude further into groove 23 such that the segment 28 of groove 23 creates an opening width 43 sized for trapping a five French catheter 13 therein. On the otherhand, as shown in FIG. 3, edge 63 protrudes a lesser distance into groove 23 in order to accommodate a ten French catheter 14 in the segment 28 of groove 23 corresponding to a different sized catheter capture channel 42. For purposes of illustration, one may consider a five French catheter as corresponding to a smaller diameter catheter size, whereas a ten French catheter might correspond to a larger diameter sized catheter. However, those skilled in the art will appreciate that the illustrated embodiment should not be interpreted as limiting the scope of the present disclosure to any particular range of catheter sizes. Thus, the present disclosure contemplates universal catheter tray assemblies 15 suitable for catheter sizes smaller than five French as well as catheter sizes larger than ten French.

Both the base tray 20 and the rotatable dials 60 may be formed from a suitable plastic such as PETG that may include a small amount of a dye color, such as blue to give the catheter tray assembly 15 a pleasing hue. Those skilled in the art will appreciate that there are many different mating surface shape configurations that would work equally well in facilitating a snap connection between the individual rotatable dial 60 and the base tray 20. In the illustrated embodiment, the snap connector feature 44 on each of the rotatable dials 60 matches and mates to a counterpart snap connector 24 formed in base tray 20.

Referring now to FIGS. 4-6, a universal catheter tray 15 according to another embodiment of the present disclosure differs from the previous embodiment in that groove 23 runs in a straight line, whereas the embodiment of FIGS. 1-3, the groove 23 defines a spiral path. In order to avoid confusion, many of the same numbers used to describe identical features are also used in relation to the embodiment of FIG. 4. Thus, universal catheter tray 15 of FIG. 4 is similar in that it includes a base tray 20 formed to include a fitting indentations 21a and 21b separated from a shaped tip indentation 22 by a groove 23. In this embodiment, two fitting indentations 21a and 21b are shown in order to illustrate that universal catheter tray 15 is made to accommodate both short and longer length catheters. In particular, universal catheter tray assembly 15 is configured with two catheter size selectors 40 attached to base tray 20 at respective locations 25 and 26 along groove 23. In this embodiment, the catheter size selectors 40 are groove inserts 50 that define catheter capture channels 42 to accommodate catheter sizes associated with the size indicia 41 formed in the groove insert 50 as best shown in FIG. 5. Groove insert 50 may include a plurality of overhang tabs 51 that help to maintain a catheter 13 of the size associated with indicia 41 trapped therein. Unlike the earlier embodiment, the snap connectors 44 for groove inserts 50 may take the form of buttons that mate to counterpart snap connectors 24 formed on base tray 20. Unlike the earlier embodiment, the catheter size selectors 40 in the form of groove inserts 50 define catheter capture channels 42 with an opening width 43 corresponding to the size indicia 41. For illustrative purposes, the Universal catheter tray assembly 15 of FIG. 4 is shown as using groove inserts 50 associated with a five French catheter 13. FIG. 6 shows a larger ten French catheter 14 which would be too large to fit in the groove insert 50. However, a different size groove insert for a ten French catheter 14 could likewise be attached to base tray 20 since the groove 23 formed in base tray 20 is substantially wide enough to accommodate any sized catheter.

Referring now to FIG. 7, an example inventory 10 is shown with a first set of catheters 11 that consists of identical small diameter catheters 13 (FIGS. 2, 5), and a second set of catheters 12 that consists of identical larger diameter catheters 14 (FIGS. 3, 6). In this illustrated example, the smaller diameter catheters 13 are five French catheters whereas the larger diameter catheters 14 are ten French catheters. Those skilled in the art will appreciate that inventory 10 includes different numbers of six French, seven French, eight French and nine French catheters as well. Each of the first set of catheters 11 are mounted in identical first catheter tray assemblies 15. The second set of catheters 12 are mounted in identical second catheter tray assemblies 16. Each of the first and second catheter tray assemblies 15 and 16 has an identical base tray 20 with catheter size selectors 40 snap connected thereto as described with regard to the embodiments of FIGS. 1 and 4, respectively. In particular, the respective catheter size selectors 40 have a size indicia 41 formed therein corresponding to the diameter size 19 of the respective catheter 13 or 14 that the size selector is in contact with. Thus, in the case of the embodiment of FIG. 1, the catheter size selectors 40 in the form of rotatable dial 60 are rotated to a first angle associated with the smaller diameter catheters 13, whereas the catheter size selectors 40 of the second catheter tray assembly 16 have their rotatable dial 60 rotated to a second angle corresponding to the ten French size indicia. Depending upon whether the base tray 20 is associated with a spiral as in FIG. 1, each of the catheter size selectors 40 are identical to each other. If utilizing the embodiment of FIG. 4, the catheter size selectors for assemblies 15 would be different from the catheter size selectors used for assemblies 16.

INDUSTRIAL APPLICABILITY

The present disclosure finds potential application where different sized catheters are packaged in different catheter tray assemblies. The present disclosure finds specific application where economies of scale will allow different sized catheters to be packaged in universal catheter tray assemblies 15 that all include an identical base tray 20. In addition, in the case of the embodiment of FIG. 1, the present disclosure finds potential application in cases where packages of different sized catheters utilize identical catheter tray assemblies 15 that differ only in how the respective catheter size selectors 40 are rotatably oriented on the identical base trays 20. Those skilled in the art will appreciate that certain catheter sizes are used and produced in greater numbers than other catheter sizes. In the prior art, different catheter tray assembly configurations were utilized for packaging different catheter sizes, leading to potential greater expense in the per item cost for the catheter sizes having lower production runs. The present disclosure addresses this issue by allowing an identical base tray 20 to be used across a line of different catheter sizes, and potentially further offers cost reduction by allowing identical catheter size selectors 40 in the case of rotatable dial 60 version shown in FIG. 1. This may allow for economies of scale to lower the per tray costs associated with each individual catheter, even in the case of the catheter sizes with smaller production runs.

In a method of utilizing the invention to package catheters, one might first select a small diameter catheter 13. A first catheter tray assembly 15 would be constructed for the smaller diameter catheter 13 by snap connecting first and second size selectors 40 to a first base tray 20. This may be repeated for any number of smaller catheter diameters. Next, when packaging larger diameter catheters, a second catheter tray assembly is constructed for larger diameter catheters 14 by snap connecting third and fourth size selectors 40 to a second base tray 20, which is identical to the first base tray utilized with the smaller diameter catheters. When this process is done with using the reversal catheter tray assembly 15 of FIG. 1, the first, second, third and fourth size selectors 40 will all be the same, but oriented on the base tray 20 at different angles. On the otherhand, in the case of the embodiment of FIG. 4, the first and second size selectors for the small diameter catheter 13 would be identical to each other, and the third and fourth catheter size selectors 40 associated with the larger diameter catheter 14 would also be identical to each other. However, the catheter size selectors 40 or groove inserts 50 for the different size catheters would be different as for the respective opening widths 43 defined by the respective size indicia's 41 formed in the groove inserts 50. In the case of the first catheter tray assemblies 15, a smaller diameter catheter is confined in first and second catheter capture channels 42 that are defined in part by the respective size selectors 40. Likewise, in the case of the second catheter tray assemblies 16, larger diameter catheters are confined in the catheter capture channels associated with the third and fourth size selectors 40. Those skilled in the art will appreciate that in the case the size selectors are dials 60, the universal catheter tray assembly 15 is set up for a specific sized catheter by dialing the respective dials 62 and angles associated with the appropriate size indicia 41. On the otherhand if groove inserts 50 are utilized, one would select groove inserts with an appropriate size indicia for packaging a catheter of the size associated with the size indicia 41. Although the present disclosure has been illustrated with the spiral packaging configuration of FIG. 1 utilizing dials 60, and the straight line configuration of FIG. 4 using groove inserts 50, dials could be used in the straight line version and groove inserts 50 could be used in the spiral version without departing from the present disclosure. In some instances associated with the spiral version, the catheters may need to be bended in order to accommodate the spiral shaped groove 23. On the otherhand in the case of the straight line version of FIG. 4, the catheters merely need to be extended in the groove 23 between the fitting and the indentation 21 and the indentation 22. As shown in dotted lines, the embodiment of FIG. 4 shows a plurality of tip shapes 70 positioned in the shaped tip indentation 22, and illustrates first and second segments 71 and 72 of a catheter 13 confined in the first and second catheter capture channels 42 defined by the groove inserts 50.

Once the catheters are mounted in the individual universal catheter tray assembly 15, the assembly is often further packaged in an outer pouch for shipping and inventory purposes. The present disclosure has the advantage of potentially eliminating multiple different size trays to accommodate different French size catheters. In addition, the present disclosure may eliminate storage space that by utilizing a common identical base tray 20 for all of the different sized catheters prior to packaging. Finally, the present disclosure offers the potential advantage of reducing costs associated with tooling for different trays, and hence may reduce the per piece tray cost for both lower and higher volume sized catheters.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A universal catheter tray assembly comprising:
   a base tray formed to include a fitting indentation separated from a shaped tip indentation by a groove, and including a first snap connector at a first location along the groove and a second snap connector at a second location along the groove;
   a first catheter size selector, which includes a size indicia formed therein, snap connected to the base tray at the first snap connector and defining at least a portion of a first catheter capture channel with an opening width corresponding to the size indicia;
   a second catheter size selector, which includes the size indicia formed therein, snap connected to the base tray at the second snap connector and defining at least a portion of a second catheter capture channel with an opening width corresponding to the size indicia; and
   wherein the tray assembly is configured for packaging a catheter with a size corresponding to the size indicia and with one of a plurality of tip shapes such that first and second segments of the catheter are confined in the first and second catheter capture channels, respectively.

2. The universal catheter tray assembly of claim 1 wherein each of the first and second catheter size selectors are rotatable dials with a plurality of size indicia formed therein;
   the dial has a plurality of detents around a rotation axis corresponding to individual ones of different catheter sizes.

3. The universal catheter tray assembly of claim 2 wherein each of the first and second capture channels is defined by an edge of the dial and a segment of the groove.

4. The universal catheter tray assembly of claim 3 wherein a centerline of the groove runs straight between the fitting indentation and the shaped tip indentation without curving.

5. The universal catheter tray assembly of claim 3 wherein a centerline of the groove runs in a spiral between the fitting indentation and the shaped tip indentation.

6. The universal catheter tray assembly of claim 1 wherein each of the first and second catheter size selectors are groove inserts that define the first and second catheter capture channels, respectively.

7. The universal catheter tray assembly of claim 6 wherein a centerline of the groove runs straight between the fitting indentation and the shaped tip indentation without curving.

8. The universal catheter tray assembly of claim 7 wherein a centerline of the groove runs in a spiral between the fitting indentation and the shaped tip indentation with curving.

\* \* \* \* \*